(12) United States Patent
Danger et al.

(10) Patent No.: US 6,186,787 B1
(45) Date of Patent: Feb. 13, 2001

(54) DENTAL INSTRUMENT

(75) Inventors: Karl-Heinz Danger, Detmold; Ralf Danger, Dörentrop, both of (DE)

(73) Assignee: Gebr. Brasseler GmbH & Co. KG, Lemgo (DE)

( * ) Notice: Under 35 U.S.C. 154(b), the term of this patent shall be extended for 0 days.

(21) Appl. No.: 09/227,093

(22) Filed: Jan. 5, 1999

(30) Foreign Application Priority Data

Jan. 7, 1998 (DE) ............................................. 198 00 324

(51) Int. Cl.⁷ ....................................................... A61C 3/02
(52) U.S. Cl. ............................................. 433/165; 408/226
(58) Field of Search ................................ 433/3, 165, 166, 433/102; 408/226, 227

(56) References Cited

U.S. PATENT DOCUMENTS

| | | | |
|---|---|---|---|
| 418,108 | * | 12/1889 | Browne ................................. 433/165 |
| 788,906 | * | 5/1905 | Homann ............................... 433/165 |
| 2,164,571 | * | 7/1939 | Christman . | |
| 2,904,313 | * | 9/1959 | Wisenbaker . | |
| 3,971,135 | * | 7/1976 | Leu ....................................... 433/165 |
| 4,019,254 | * | 4/1977 | Malmin ................................. 433/102 |
| 5,080,588 | * | 1/1992 | O'Brien ................................ 433/165 |
| 5,429,504 | * | 7/1995 | Peltier et al. ......................... 433/165 |
| 5,762,497 | * | 6/1998 | Heath .................................... 433/102 |
| 5,857,852 | * | 1/1999 | Garman ................................. 433/102 |
| 5,873,719 | * | 2/1999 | Calms et al. ......................... 433/165 |
| 5,876,202 | * | 3/1999 | Berlin ................................... 433/165 |
| 5,882,198 | * | 3/1999 | Taylor et al. ......................... 433/102 |
| 5,975,899 | * | 11/1999 | Badoz et al. ......................... 433/102 |

FOREIGN PATENT DOCUMENTS

| | | | |
|---|---|---|---|
| 584316 | * | 2/1933 | (DE) ..................................... 433/166 |
| 1541216 | | 3/1970 | (DE) . |
| 361315 | * | 11/1931 | (GB) ..................................... 433/165 |
| 1132876 | | 2/1966 | (GB) . |

* cited by examiner

Primary Examiner—Ralph A. Lewis
(74) Attorney, Agent, or Firm—Shinjyu Global IP Counselors, LLP

(57) ABSTRACT

A dental instrument is provided with a pivotally arranged shaft and a head mounted to the shaft. The head is equipped with a plurality of cutting blades. The cutting blades have a clearance angle of 0° and a negative cutting angle. The areas of the blades that trail the cutting edges are either planar surfaces or a partially cylindrical shape. In some embodiments, the front area of head is provided with a circumferential groove that is open at the front side, into which an annular contact element (O-ring) is inserted. The contact element can have the shape of an elastic ring.

21 Claims, 2 Drawing Sheets

DENTAL INSTRUMENT

BACKGROUND OF THE INVENTION

1. Field of the Invention

This invention generally relates to dental instrument. More specifically, the present invention relates to dental instrument with a pivotally arranged shaft and a head mounted to the shaft. The head is equipped with a plurality of cutting blades.

2. Background Information

In regulating teeth, it is a common measure in orthodontics to adhere so-called brackets to the teeth in place of braces. The brackets are subsequently connected with each other by means of wires. These brackets and wires apply forces to the teeth, which cause a change of position of the teeth. The brackets, which are mostly made of metal, are secured by means of specific synthetic materials. Of course, the brackets adhered to the tooth surface are to be removed when the orthodontic treatment is concluded. However, this also requires the removal of all adhesive residues from the tooth surface.

The problem of clearing away the adhesive or the residual adhesive from the tooth surface does not only exist for the orthodontist but also for the after-treating dentist whose main work is the removal of the residual adhesive. It is mainly during the removal of these residues where care must be taken that the tooth surface and the dental enamel are not being damaged.

The common rotating dental instruments known from the state of the art are only conditionally suitable for the removal of adhesive residues as the tooth surface and/or the tools will abrade the dental enamel. Also, the tooth may be damaged as a result of an inferior contact, e.g. when the residual synthetic material has been removed or when the tool slips.

In view of the above, there exists a need for dental instrument which overcomes the above mentioned problems in the prior art. This invention addresses this need in the prior art as well as other needs, which will become apparent to those skilled in the art from this disclosure.

SUMMARY OF THE INVENTION

The invention is based on the problem of providing a dental instrument of the initially mentioned kind which allows a simple and safe employment for reliably removing residual adhesive without damaging the tooth surface.

According to the present invention, a dental instrument with the features of the main claim solves the above-mentioned problem. The subclaims recite further advantageous embodiments of the present invention.

The present invention provides that the dental instrument that comprises a shaft and a head attached thereto. The head comprises a plurality of cutting blades attached thereto. The cutting blades are designed such that the blades have a clearance angle of 0°. A clearance angle of 0° as used herein means that the blade has an external surface, relative to the envelope curve of the dental instrument, by means of which the dental instrument can be propped onto the surface of the tooth or abutted against it. A rotating movement of the instrument thus leads to a substantially damage-free contact with the tooth surface. The beveled circumferential areas of the blades thus are supported by the tooth surface. On the other hand, residual adhesives projecting from the tooth surface are removed reliably.

According to the present invention, the areas of the blades are each provided with a clearance angle that can be of plane or partially cylindrical shape. In any case, the areas of the blades have sufficient surface for contacting the tooth surface without causing damage.

For processing and removing the residual synthetic material, it is favorable according to one of the embodiments of the invention that each of the blades has a negative cutting angle.

Moreover, the dental instrument of the present invention can comprise a plurality of blades, which are arranged substantially in parallel to each other. The shape of the head can be adapted to each condition of use. For example, the shape of the head can be realized as cylindrical, conical, ball-like or other shapes. The blades can run in a straight or screwed and/or spiral way.

The dental instrument according to the present invention can also be constructed such that it can be used for clockwise and counterclockwise rotation. It this case it might be favorable to make the blades symmetrically, relative to a plane running substantially through the rotational axis of the shaft. Of course, the symmetry is evident, in particular from individual vertical cuts through the rotational axis of the head of the dental instrument.

In order to guarantee an even and reliable removal of the residues of adhesive and/or synthetic material, it may be favorable to construct the blades equally. However, it is also possible to provide blades of different geometry at the circumference of the dental instrument. In particular, those types of blades have different cutting angles.

It is self-evident that with the dental instrument of the present invention, the dentist has to exert a certain contact pressure onto the surface of the tooth to be treated for removing the residual synthetic material. In particular larger amounts of synthetic material must be cleared away layer by layer. In order to create a contact possibility and in order to allow a well aimed exertion of the contact pressure, it may be favorable that the head comprises at least one annular, elastically deformable contact element projecting beyond the head's envelope curve. This allows the dentist to abut the contact element to the tooth surface before pressing the dental instrument against the tooth surface by elastically deforming the contact element, in order to remove the residual synthetic material.

It is particularly favorable when the contact element has the shape of a ring inserted into a circumferential groove of the head, e.g. like an O-ring. The circumferential groove can be provided at the front end or free end of the head or at any other section thereof. Of course, it is also possible to provide a plurality of circumferential grooves with a plurality of contact elements.

The contact element can have the shape of an elastic ring and it can be made from silicon or other synthetic materials. Due to the elasticity of its material, the contact element can be removed from the dental instrument in simple manner, e.g. for cleaning or sterilizing it.

These and other objects, features, aspects and advantages of the present invention will become readily apparent to those skilled in the art from the following detailed description, which, taken in conjunction with the annexed drawings, discloses preferred embodiments of the present invention.

BRIEF DESCRIPTION OF THE DRAWINGS

Referring now to the attached drawings which form a part of this original disclosure.

Similar reference characters denote corresponding features consistently throughout the attached drawings.

DETAILED DESCRIPTION OF THE PREFERRED EMBODIMENTS

Figure 1:
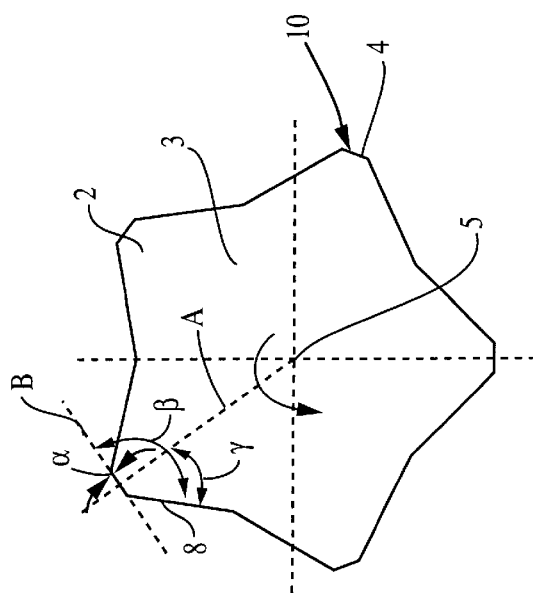
FIG. 1 shows a schematically simplified sectional view of a dental instrument according to one embodiment of the present invention.
Figure 2:
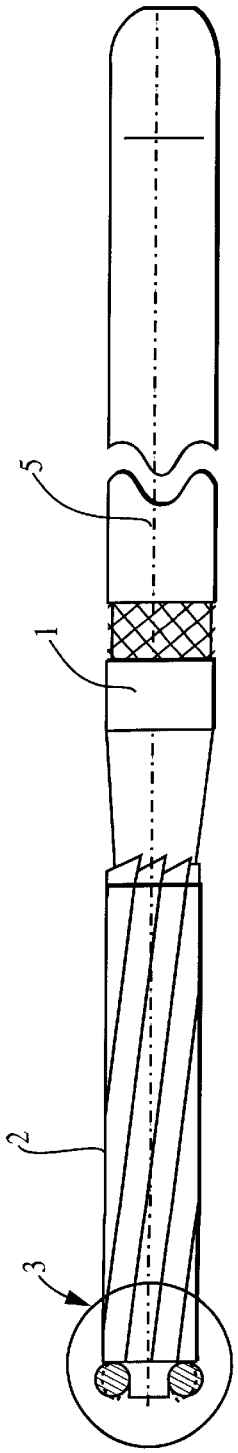
FIG. 2 shows a side view of an example of the dental instrument according to another embodiment of the present invention.
Figure 5:
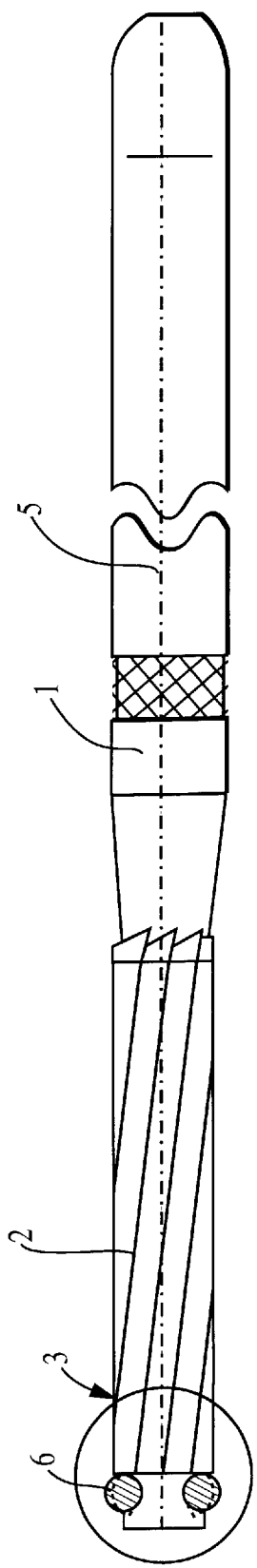
FIG. 5 shows a side view of a further example of the dental instrument according to the present invention, analogous to the representation of FIG. 2.

FIG. 1 shows a simplified sectional view through a head 3 of an example of the dental instrument according to the present invention. The head 3 is preferably integrally connected with a shaft 1, in the same manner as illustrated in the embodiments of FIGS. 2 and 5. The head 3 of the dental instrument is rotatable around a central rotational axis 5 of shaft 1. As known from the state of the art, shaft 1 can be connected with a drive means in common manner to rotate shaft 1 and head 3 about axis 5. Making reference to the state of the art can thus dispense with a detailed description of shaft 1.

Basically, the present invention relates to a dental instrument with a rotatably arranged shaft 1 with head 3 mounted to one end of the shaft 1. The head 3 is equipped with a plurality of cutting blades 2. The cutting blades 2 have longitudinally extending cutting edges that are preferably parallel to each other and to the central rotational axis 5 of shaft 1. Each cutting blade 2 has at least one cutting edge 10, a first surface 4 with an externally facing surface area and a second surface 8. The cutting blades 2 have cutting edges with a clearance angle ($\alpha$) of 0° relative to the central rotational axis 5 of shaft 1. A clearance angle ($\alpha$) of 0° as used herein means that the cutting edge of the blade 10 is followed by an external surface area 4 extending in the circumferential direction, relative to the envelope curve of the dental instrument, by means of which the dental instrument can be propped onto the surface of the tooth or abutted against it. A rotating movement of the instrument thus leads to a substantially damage free contact with the tooth surface. The beveled circumferential areas of the blades 2 thus are supported by the tooth surface. On the other hand, residual adhesives projecting from the tooth surface are removed reliably.

The example shown in FIG. 1 comprises five cutting blades 2. Each of the cutting blades 2 has a cutting angle ($\gamma$), a clearance angle ($\alpha$) and a wedge angle ($\beta$) as seen in FIG. 1. These three angles are defined relative to reference lines A and B. In particular, the first radial reference line A is drawn from the axis of rotation 5 through the leading cutting edge of blade 2, while the second tangential reference line B is drawn perpendicular to the first reference line A and through the leading cutting edge of blade 2. If rotated counterclockwise, as shown in the drawing, the blades 2 are formed with negative cutting edges or angles ($\gamma$) as seen in FIG. 1. The cutting angle ($\gamma$) is the angle formed between reference line A and the forward or second cutting surface 8. The pertaining clearance angle ($\alpha$) is 0° for the cutting blades 2 as seen in FIG. 1. The clearance angle ($\alpha$) is the angle formed between the trailing surface or area 4 and reference line B. The wedge angle ($\beta$) is the angle formed between the cutting angle ($\gamma$) and the clearance angle ($\alpha$). For each blade 2, the sum of these three angles equals 90°, where the cutting angle ($\gamma$) is expressed as a negative cutting angle.

As evident from FIG. 1, an external area 4 of each blade 2 forms a plane or a partially cylindrical contact surface, by means of which the dental instrument can prop onto the surface of a tooth. Moreover, the dental instrument of the present invention can comprise a plurality of blades 2, which are arranged substantially in parallel to each other. The shape of the head can be adapted to each condition of use. For example, the shape of the head can be realized as cylindrical, conical, ball-like or other shapes. The blades can run in a straight or screwed and/or spiral way. In any case, the areas of the blades have sufficient surface for contacting the tooth surface without causing damage.

It is self-evident that the head 3 of the dental instrument according to the present invention can be constructed in different manners. The blades 2 can also be arranged in convergent or divergent relation to one another. Accordingly, the widths of areas 4 can vary over the length of the blades 2.

FIGS. 2 to 6 show two further examples of the dental instrument according to the invention. For clarification of the representation, a still increased enlargement of the areas 4 of blades 2 as shown in FIG. 1 was dispensed with. As already explained above, the areas 4 can be of different widths within the scope of the invention.

In the example of FIGS. 2 and 5, the head 3 is of substantially cylindrical shape and comprises a plurality of spiral blades 2. Blades 2 are arranged in parallel relation to one another. Twelve blades 2 are formed on head 3 as shown in FIG. 2.

Figure 4:
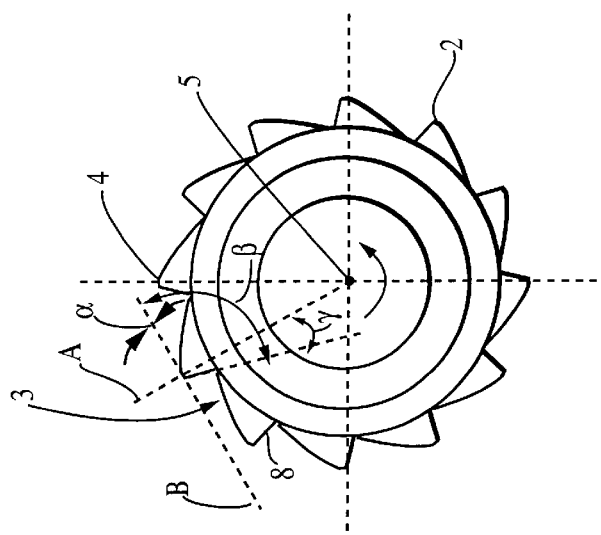
FIG. 4 shows a front view of the dental instrument according to FIGS. 2 and 3.
Figure 3:
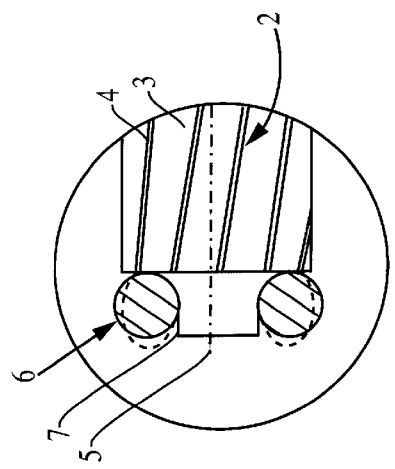
FIG. 3 shows an enlarged representation of the detail shown in FIG. 2.

The example of FIGS. 2 to 4 shows that the front area of head 3 is provided with a circumferential groove 7 which is open at the front side, into which an annular contact element 6 (O-ring) is inserted. The contact element 6 can have the shape of an elastic ring and it can be made from silicon or other synthetic materials. Due to the elasticity and resiliency of its material, the contact element 6 can be removed from the dental instrument in simple manner, e.g. for cleaning or sterilizing it. In an undeformed state, the undeformed contact element 6 extends beyond the envelope curve of said head 3, so that when the dental instruments is propped onto the surface of a tooth the contact element 6 contacts the surface of the tooth first. With an increasing contact pressure the contact element 6 deforms as shown by dotted lines in FIG. 3. With a respective deformation of the contact element 6, the blades 2 come into contact with the surface of the tooth, thus allowing blades 2 to clear off the residual synthetic material.

FIG. 4 shows a front view of head 3, from which it is evident that the blades 2 are not constructed symmetrically (cp. with the example of FIG. 1). The areas 4 of the blades 2 that have a clearance angle ($\alpha$) of 0° are rather small. In other words, the areas 4 have small widths. As best seen in FIGS. 2 and 3, the areas 4 of the blades 2 are spiral areas that are parallel to each other. The areas 4 of the blades 2 are either planar surfaces as in FIG. 1 or a partially cylindrical shape as in FIG. 4.

Figure 6:
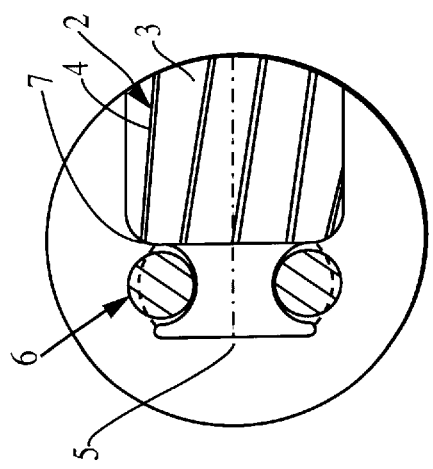
FIG. 6 shows an enlarged representation of the detail of FIG. 5.

The example shown in FIGS. 5 and 6 differs from the example of FIGS. 2 to 4 by the shape of the circumferential groove 7, which is no longer open at the front side, so that the annular contact element 6 is supported at both sides. This also changes the deformability of the contact element 6 (see dotted lines of FIG. 6).

While several embodiments have been chosen to illustrate the present invention, it will be apparent to those skilled in the art from this disclosure that various changes and modifications can be made herein without departing from the scope of the invention as defined in the appended claims. The present invention is not restricted to the example shown, rather there exists many possibilities for variations and modifications within the framework of the present invention. Furthermore, the foregoing description of the embodiments according to the present invention are provided for illustration only, and not for the purpose of limiting the invention as defined by the appended claims and their equivalents.

What is claimed is:

1. A dental instrument comprising a rotatably arranged shaft having a first end and a second end with a longitudinal rotational axis extending between said first and second ends, and a head coupled to said shaft for rotation about said rotational axis of said shaft with said shaft and said head being so dimensioned to be used to remove material from a tooth, said head being equipped with a plurality of at least five cutting blades, each of said cutting blades having a cutting edge facing in a first rotational direction, a first surface extending in a first rotational direction from said cutting edge and a second surface extending in a second opposite rotational direction from said cutting edge, each of said cutting edges is followed by a planar external surface area of said first surface in said first rotational direction to form a clearance angle of 0° for each of said cutting edges so that said external surfaces can be propped onto a tooth surface.

2. The dental instrument according to claim 1, characterized in that each of said second surfaces of said blades forms a negative cutting angle relative to a reference line passing through said rotational axis and said cutting edges.

3. The dental instrument according to claim 2, characterized in that said plurality of blades are arranged in substantially parallel relation to each other.

4. The dental instrument according to claim 2, characterized in that said blades are symmetrical to a plane encompassing said rotational axis of said shaft.

5. The dental instrument according to claim 2, characterized in that said blades are identical to each other.

6. The dental instrument according to claim 1, characterized in that said plurality of blades are arranged in substantially parallel relation to each other.

7. The dental instrument according to claim 6, characterized in that said blades are symmetrical to a plane encompassing said rotational axis of said shaft.

8. The dental instrument according to claim 6, characterized in that said blades are identical to each other.

9. The dental instrument according to claim 1, characterized in that said blades are symmetrical to a plane encompassing said rotational axis of said shaft.

10. The dental instrument according to claim 1, characterized in that said blades are identical to each other.

11. A dental instrument comprising a rotatably arranged shaft having a first end and a second end with a longitudinal rotational axis extending between said first and second ends; and a head coupled to said shaft for rotation about said rotational axis of said shaft said head being equipped with a plurality of cutting blades each of said cutting blades having a clearance angle of 0°, said head comprising at least one annular elastically deformable contact element extending beyond an envelope curve formed by said cutting blades of said head.

12. The dental instrument according to claim 11, characterized in that each of said cutting blades has a cutting edge, a first surface extending in a first rotational direction from said cutting edge, a second surface extending in a second opposite rotational direction from said cutting edge, and a planar external surface following said cutting edge.

13. The dental instrument according to claim 11, characterized in that each of said cutting blades has a cutting edge, a first surface extending in a first rotational direction from said cutting edge, a second surface extending in a second opposite rotational direction from said cutting edge, and an external surface with a partially cylindrical shape following said cutting edge.

14. The dental instrument according to claim 11, characterized in that said cutting blades have a negative cutting angle.

15. The dental instrument according to claim 11, characterized in that said plurality of blades are arranged in substantially parallel relation to each other.

16. The dental instrument according to claim 11, characterized in that said blades are symmetrical to a plane encompassing said rotational axis of said shaft.

17. The dental instrument according to claim 11, characterized in that said blades are identical to each other.

18. The dental instrument according to claim 11, characterized in that said contact element has the shape of an O-ring inserted into a circumferential groove of said head.

19. The dental instrument according to claim 18, characterized in that said contact element is arranged at a front end of said head that is opposite said shaft.

20. The dental instrument according to claim 11, characterized in that said contact element is arranged at a front end of said head that is opposite said shaft.

21. A dental instrument comprising:

a rotatably arranged shaft having a first end and a second end with a longitudinal rotational axis extending between said first and second ends; and a head having a free end a fixed end coupled to said shaft for rotation about said rotational axis of said shaft, said bead being equipped with a plurality of cutting blades, said head comprising at least one annular elastically deformable contact element extending beyond an envelope curve formed by said cutting blades of said head, said contact element being coupled to said free end of said head such that said cutting blades are located entirely between said contact element and said fixed end of said head.

* * * * *